United States Patent [19]

Tretiakoff et al.

[11] 4,305,067
[45] Dec. 8, 1981

[54] ELECTROMECHANICAL TRANSDUCER FOR RELIEF DISPLAY PANEL

[76] Inventors: Oleg Tretiakoff; Andree Tretiakoff nee Asseo, both of 43, avenue Lulli, 92330 Sceaux, France

[21] Appl. No.: 825,116

[22] Filed: Aug. 16, 1977

Related U.S. Application Data

[63] Continuation-in-part of Ser. No. 605,853, Aug. 19, 1975.

[30] Foreign Application Priority Data

Aug. 22, 1974 [FR] France .................... 74 28793
Aug. 5, 1977 [FR] France .................... 77 24320

[51] Int. Cl.³ ............................................ G06F 3/14
[52] U.S. Cl. .................................. 340/407; 340/700; 434/114
[58] Field of Search ............... 340/407, 336, 700, 756, 340/806; 35/35 A; 310/311; 248/1; 403/391, 389, 395, 400

[56] References Cited

U.S. PATENT DOCUMENTS

| | | | |
|---|---|---|---|
| 3,229,387 | 1/1966 | Linvill | 310/311 |
| 3,360,883 | 1/1968 | Glanzer | 403/391 |
| 3,659,354 | 5/1972 | Sutherland | 35/35 A |
| 3,932,869 | 1/1976 | Kane | 35/35 A |
| 4,044,350 | 8/1977 | Tretiakoff et al. | 340/336 |

*Primary Examiner*—Marshall M. Curtis
*Attorney, Agent, or Firm*—Edwin E. Greigg

[57] ABSTRACT

A reading plate has an array of holes in its surface. Rounded ends of rods project selectively through these holes by the action of a set of bimorphous piezoelectric reeds, to which they are coupled. Each reed is connected to a source of electric voltage which can assume two distinct values as a function of an electrical control signal in order to make the piezoelectric reeds bend in one direction or the other. The reading rods are distributed in groups of six and arranged in each group according to the conventional arrangement of dots of a braille character. The transducer can thus provide a relief read-out panel for a pocket electronic calculator for the blind. Methods of using these transducers for recording and readout of magnetic tape with data in Braille-generable form and equipment incorporating them are disclosed.

17 Claims, 3 Drawing Figures

ELECTROMECHANICAL TRANSDUCER FOR RELIEF DISPLAY PANEL

This is a continuation-in-part of our copending U.S. Patent application Ser. No. 605,853 filed Aug. 19, 1975, the subject matter of which is herein incorporated by reference.

BACKGROUND OF THE INVENTION

1. Field of the Invention

This invention relates to novel electromechanical transducer devices for relief display panels, to methods of using these and to equipment incorporating them.

The invention relates generally to reading and monitoring apparatus for the blind and more particularly to methods and devices for converting data into and/or from tactual symbols, such as Braille.

Electronic pocket calculators could be of immense service to the blind who encounter the greatest difficulty in making numerical calculations, especially when these calculations require the use of magnitudes which must be sought in tables (for example logarithms, trigonometric functions, etc.).

Such calculators are at present useless to blind persons since the results are presented in the form of a visual image e.g. luminous figures in a window.

In the Braille system, each sign (letter, figure or sign of punctuation) is represented by a geometric figure constituted of points in relief to a maximum number of six. These geometric figures are easily recognized to the touch by the blind who can, with training, read very rapidly. Unfortunately, braille books are heavy, bulky and expensive to produce, which limits the access of blind people to written information.

2. Description of the Prior Art

To overcome these drawbacks and to produce texts in relief from electrical signals, electromechanical methods are known enabling the production of Braille characters in relief. The known methods have all numerous drawbacks: mechanical complexity, bulk, weight, noise, high consumption of electricity.

More recently, it has been proposed to use vibrating points with piezoelectric actuation to constitute characters intended to be read by touch (U.S. Pat. No. 3,229,387). This device has, however, serious drawbacks. Firstly, the majority of blind people find their sense of touch fatigued and even irritated by the vibrations. Furthermore, they are obliged to adapt themselves to a mode of reading which is very different from that of books in relief: instead of drawing the finger over a line of characters in relief, thereby being able to slow down, accelerate, stop or back-track at will, they must—by reason also of fragility of the vibrating points—leave the finger immobile on the vibrating points, the latter then successively presenting the characters of the text. Lastly, the vibrating points emit a distinctly audible sound, which then constitutes a nuisance in the vicinity particularly if several persons work close together.

GENERAL DESCRIPTION OF THE INVENTION

It is an object of the invention to provide an electromechanical transducer device which enables graphic or pictorial contours or profiles to be represented in modifiable relief displays.

Another object of the present invention to provide a display device presenting to a person reading tactually (who may be sighted or blind), lines of characters in relief with characteristics identical to those that they are accustomed to encounter in Braille books of the best quality.

Another object of this invention is to provide a silent and vibration-free relief display device.

It is a further object of the invention to provide an improved method of recording written printed or relief characters on magnetic tape including the step of monitoring the recording tactually by means of an improved relief read-out display.

It is also an object of the invention to provide an improved method of readout of magnetic tape bearing data in Braille-generable form including the step of monitoring the recording tactually by means of an improved relief readout display.

Yet another object is to provide a method of readout of magnetic tape bearing data in Braille-generable form in predetermined accumulations of characters.

Another object is to provide a magnetic tape bearing data adapted to generate a display in Braille characters produced by an improved method; it is also an object to provide such a Braille-generable magnetic tape in standard cassette form.

These and other objects of this invention may be achieved by means of an electromechanical transducer device comprising: a bimorphous piezoelectric reed bendable around an axis perpendicular to the longitudinal axis of the reed on application to said reed of a DC voltage; support means for at least one end of said reed; coupling means supported on said reed; a rod coupled to said piezoelectric reed through said coupling means; means for applying a DC voltage to said reed; whereby on the application of said voltage the bending movement of the reed is translated into static displacement of said rod in the direction of its own longitudinal axis.

According to a particularly useful application of the invention, a panel for forming a relief image comprises: a tactually scannable plate having a plurality of holes therethrough arranged in an array; a plurality of rods having corresponding ends traversing slidably said holes; a plurality of bimorphous piezoelectric reeds arranged on one side of said plate; means for supporting the ends of said reeds and means for electrical connection to the electrodes of said reeds; rod-coupling means supported on each said reed and coupling each rod to a respective one of said piezoelectric reeds; each rod being thereby movable along its longitudinal axis between a first static position in which its said end projects a tactually detectable distance from its hole and a second static position in which its said end does not project from its hole, by the application of a DC voltage to its respective reed.

In an electronic calculator, constructed according to the present invention, the results can be presented in the form of Braille figures in relief, appearing in a window similar to that of ordinary pocket calculators. In these calculators, the actuating keyboard can include several tens of keys each for actuating a different operation: entry of a figure into the calculator, addition, subtraction, multiplication, division, root extraction, etc. . .

In a calculator according to the present invention, each of the possible operations is actuated by composing a Braille character by means of a seven-keyboard similar to that of a Braille typewriter.

According to another aspect of the invention there is provided a method of recording written or printed characters onto magnetic tape including the step of monitoring the recording comprising: sending signals generated from said characters adapted for recording on the magnetic tape, to a relief display device comprising a support housing including a tactually scanable plate having a plurality of holes therethrough arranged in an array; a plurality of electromechanical transducer devices housed in said housing, each electromechanical transducer device comprising a bimorphous piezoelectric reed bendable longitudinally on the application of a DC voltage, support means for each end of said reed, coupling means supported on said reed, and a rod arranged transversely to said piezoelectric reed and coupled to said coupling means, said rod having an end traversing slidably a respective corresponding one of said holes between a first static position in which said rod end projects a tactually detectable distance from its hole and a second static position in which said rod end does not project from its hole, by the application of a DC voltage to said reed; and a printed circuit adapted to be held against said housing, bearing a plurality of electrical actuating circuits for the respective piezoelectric reeds.

Preferably said method comprises the steps of (1) feeding said tape through a magnetic tape read-out head to generate signals, (2) sending said signals to a decoding interface, (3) sending said decoded signals to a memory until there is a predetermined accumulation of characters, and (4) sending said accumulation of characters to said relief display device.

According to another aspect of the invention a method of readout of magnetic tape bearing data in Braille-generable form comprises the aforementioned steps (1) to (4).

By the aforesaid methods according to the invention these are provided magnetic tapes bearing data adapted to generate a display in Braille characters, preferably in standard cassette form.

According to a preferred embodiment of the invention the aforementioned rod-coupling means for the novel relief display device comprises a generally rectangular tablet, of insulating material, said tablet defining a plurality of holes traversing the tablet perpendicular to its two largest surfaces one of said holes being tapped to engage a corresponding thread formed on one of said rods, the rest of said holes being freely traversible by the other rods, and a slot communicating the tapped hole to one of the smaller surfaces of the tablet, so as to provide a gripping effect of the perimeter of the tapped hole on the threaded rod.

The invention further includes the method of fabricating such a rod-coupling means, comprising first forming said slot in the tablet and then forming the tapped hole. The slot may be formed by molding or by cutting.

According to another preferred embodiment of the invention, the thread on said threaded rod is formed by knurling.

BRIEF DESCRIPTION OF THE DRAWINGS

Further objects and advantages of the invention will become apparent from the following description of various embodiments given purely by way of illustrative but non-limiting example taken in conjunction with the accompanying drawings, in which.

DESCRIPTION OF SPECIFIC EMBODIMENTS

Figure 1:
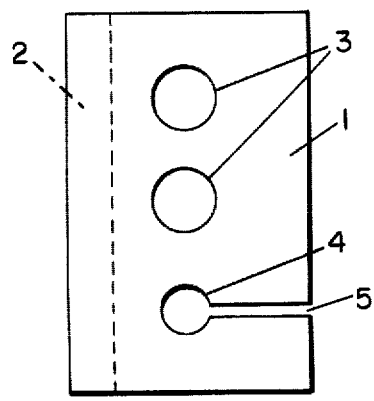
FIGS. 1 and 2 show an embodiment of a rod-coupling means for an electromechanical transducer device according to the invention in plan view and end view respectively.
Figure 2:
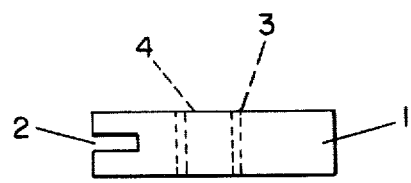

Referring to FIGS. 1 and 2, the rectangular block or tablet 1 constitutes one of the coupling means for coupling a rod to a respective piezoelectric reed. The tablet has a groove 2 passing throughout its longest edge wherein the piezoelectric reed can rest horizontally. The rod has three holes passing through it perpendicular to its largest surfaces and located close to the groove 2. Two of the holes 3 are of a diameter which enables the rods to pass freely therethrough. The third hole 4 is tapped to engage a threading on the rod passing through it, said rod having means for rotating it round its axis, such as a slot at either end of the rod, to facilitate adjustment of the projection of the rounded end of the rod above the upper surface of the support on the display panel (not shown). A slot 5 connects the tapped hole 4 to a long edge of the tablet. Preferably the width of this slot 5 is less than a quarter of the diameter of the tapped hole 4. The effect of the slot is to greatly facilitate the smoothness and firmness of the grip between the tapping of the tablet and the threads on the rod.

To form the slotted threaded hole 4 satisfactorily, it has been found desirable to first form the slot in the tablet and then to tap the tapped hole.

It is also found to be desirable to form the thread on the threaded rod by knurling.

The material constituting the tablet must be an excellent insulating material since the inner surfaces of the grooves are in contact with the electrodes of the piezoelectric strip between which a potential difference of several hundred volts is applied.

The material constituting the tablet must also possess a suitable elasticity (modulus of rigidity between 10,000 and 20,000 kg/cm$^2$) to ensure adequate gripping of the threaded rod in the tapped hole. The material must also be sufficiently hard (breaking strength greater than 500 kg/cm$^2$) to enable the tapping of the already slotted hole and the insertion of the threaded rod and it must be capable of holding up for some thousands of hours without failure.

Figure 3:
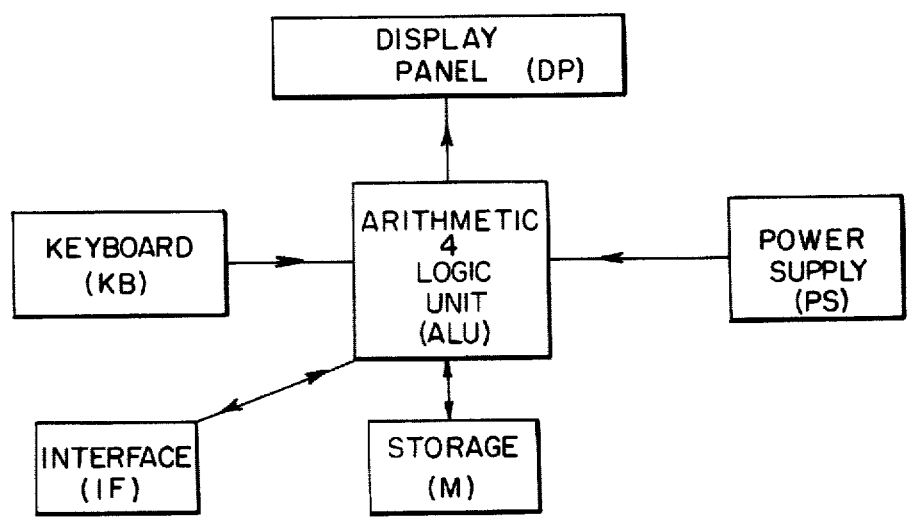
FIG. 3 is a block diagram of an embodiment of a system for performing the method of recording written or printed characters on to magnetic tape or of readout of magnetic tape bearing data in Braille-generable form according to the invention.

Referring now to FIG. 3, this shows a general arrangement of a system for recording written or printed characters on to a magnetic tape and for readout of magnetic tape bearing data in Braille-generable form, incorporating a display device according to the invention. In the embodiment shown in FIG. 3, the arrangement is analogous to that described in the embodiment of FIG. 1 in the above-mentioned copending application. However, the arithmetic unit AU in the latter is replaced by an arithmetic and logic unit ALU. The latter is connected on the one hand, to a memory system M, and on the other hand, to an input-output interface IF. In this case the keyboard KB includes in addition to the six Braille keys and the spacing key, one or several additional keys enabling the operation of the arithmetic and logic unit ALU. Thus for example there can be a key for the transfer of characters from the keyboard KB to the memory system M, to the display panel DP and to the input-output interface IF, transfer of characters from the memory system M to the display panel DP and to the interface IF, and transfer of characters from the interface IF to the memory system M and to the display panel DP. In particular, the memory system M can include a recording-readout device for magnetic tape, in particular in mini-cassettes which are easy to handle.

The device shown diagrammatically in FIG. 3 can constitute either a simple Braille recording-readout system even without the interface IF, or a true Braille terminal capable of transmitting and receiving messages when it is provided with the interface IF. The conversion of codes from or into Braille previously effected by coding CO and decoding DCO circuits, are effected by the arithmetic and logic unit ALU. In the present state of the art, this unit is preferably constituted by a microprocessor.

A system such as just described can be incorporated in a portable Braille recorder of about book size and weighing only about 4 lbs. A standard C-90 minicassette can have recorded on it by means of the device according to the invention 300,000 Braille characters (150,000 on each side) which is equivalent to a 220 page paperback book or to 6 normal Braille volumes. Sound can be recorded on the same tape as the Braille and a switch can be incorporated allowing immediate changeover from sound to Braille or vice versa on the same tape and also a microphone and loud speaker so that the device can be used as an ordinary cassette sound recorder/player.

An electronic calculator can be simply connected to the Braille recorder and the calculator can be controlled either by its own keyboard or by the Braille keyboard of the Braille recorder. In the latter case, the orders given to the calculator can be read immediately on the Braille display device and the results of the calculations are displayed in Braille on the display device as well as on the visual display of the electronic calculator.

An electric typewriter such as the IBM 82-C can be equipped with an electromagnetic driving system and with an interface which allows it to be controlled or to control directly the Braille recorder. Any sighted typist, who need know nothing about Braille, can then type a text normally on this typewriter, and each key struck will be recorded at the same time in Braille on the buffer memory of the Braille recorder. At the end of a line of 120 characters, the return to the following line automatically produces the recording on to the cassette tape of the line which has just been typed.

A blind person can type a text in Braille on the keyboard of the Braille recorder and this text will be typed at the same time in ordinary characters on a sheet of paper in the IBM electric typewriter. A text can also be typed in ordinary characters automatically from a tape previously recorded in Braille.

If two or more Braille recorders are connected together, it is possible to control all of them from any one and transfer tapes in Braille from the tape of one recorder to the tapes of all the others.

A standard interface can be used to convert Braille characters for read/write operations to and from the Braille recorder into an asynchronous stream of serial characters which conform to the international standards. The speed of transmission as well as the code used by the external device can be selected by the user. The maximum average transmission speed is 60 characters per second. The Braille recorder then constitutes a portable Braille terminal which gives a blind person a highly effective way to work with large computers. A blind computer programmer could, for example, write his programme on the Braille recorder, read it back, make corrections at will, and then switch his Braille recorder through an appropriate output connection to a large computer. The programme would then be transferred directly to the computer.

Such an interface is directly connectable to standard modems allowing the performance of all these operations over long distances by means of telephone lines or specialised networks.

A dialogue between a sighted person using a standard teletypewriter and a blind person using a Braille recorder terminal can be arranged without difficulty. Telex messages, for instance, can be received and recorded directly in Braille on a cassette.

In the previously described embodiments of the electromechanical transducer device according to the invention, the geometrical arrangement of the piezoelectric strips and the rods result in the bulk of a module representing a Braille characters perpendicular to the line of modules, cannot be less than the length of the piezo-electric strips used. Consequently, if it is desired to juxtapose two lines of Braille characters one below the other, the spacing of said lines is at least equal to the length of the strips, which is much greater than the conventional spacing of the lines in Braille books. Embodiments will now be described which enable notably the elimination of this drawback and the use of shorter strips whilst preserving the advantages of actuation by the piezoelectric strips with an amplitude of movement and a stiffness of the display elements similar to those in the previous embodiment.

Such an embodiment is characterised in that it comprises two bimorphous piezoelectric strips substantially parallel between themselves and each having one end fixed and one end pivoted to a linkrod, the free ends of the two linkrods being pivoted together, whilst a voltage source capable of taking at least two distinct values is connected to the strips so as to be able to establish at least one potential difference between the electrodes of the two opposite surfaces of the strips and the electrodes of the two facing surfaces so that this potential difference results in inward or outward curvatures of the strips and hence a movement of the common pivoting point of the link rods to which a display element rod can be fixed or pivoted.

A particular embodiment in which the common articulation point of the linkrods can take two distinct positions is characterised in that the voltage source is arranged so as to apply two opposite voltage differences so that one position corresponds to a curvature of the strips towards one another and the other position to the reverse curvature.

However in this case, each position is obtained by a certain potential difference which must be maintained. Another embodiment according to the invention is characterised in that two positions are marked by the situation at the common point of articulation of the linkrods respectively on one side or the other of the plane perpendicular to the strips and passing through the articulation points of said strips to the linkrods whilst the voltage source and its connections are arranged so as to establish a potential differnce or not between the electrodes of the strips to curve the latter in opposite direction, this voltage difference only being established during the movement of said articulation point so that the latter passes from one position to the other on each establishment of a potential difference. Thus the strips are only incurved during the movement or part of the latter and resume their resting position towards the end of the movement. In this case, the potential difference is cancelled at the latest at the moment when the speed of the common articulation point of the links and of the assembly, that it drives, becomes nil.

The piezo-electric strips can be arranged vertically and it is clear that then, their horizontal bulk is reduced to the minimum. The rods are distributed in groups of six and arranged in each group according to the conventional arrangement of Braille code dots; the device can comprise several lines of such groups.

It is also possible to distribute the perforations and the pins arranged in rows and columns regularly so as to constitute a network of tips capable of producing any type of relief pattern with good resolution by means of selective control of said tips.

It is clear that the invention is in no way limited to this application, but can on the contrary be used in any sort of apparatus which necessitates movements of small amplitude and which requires good silence in operation.

The above-mentioned features enable the production of modular Braille characters with a bulk in height less than 50 mm and geometrically identical with those of conventional Braille books. In addition, the said characters can be juxtaposed in several lines of any length and thus form a page.

Thus the device described enables also the production of a regular network of relief tips actuated electrically to constitute drawings which can be sensed by the blind. Such an arrangement constitutes a tactile equivalent of a cathode ray screen with, for example, a vertical and horizontal resolution of about 2.5 mm.

It will be apparent that although the invention has been mainly illustrated by binary signals recorded on magnetic tape, other data storage systems could be used, various other tactical characters than Braille could be displayed, for example, graphs, profiles, etc. using suitably juxtaposed mechanical linkages for the rods. These and other changes may be made in the specific embodiments described without departing from the spirit and scope of the invention, which is defined in the claims.

We claim:

1. In an electromechanical transducer device comprising:
   a bimorphous piezoelectric reed bendable around an axis perpendicular to the longitudinal axis of the reed on the application of a DC voltage;
   support means for each end of said reed;
   coupling means supported on said reed;
   a rod arranged transversely to said piezoelectric reed and coupled to said coupling means;
   and means for applying a DC voltage to said reed whereby on the application of said voltage the bending of the reed causes displacement of said rod in the direction of its own longitudinal axis from a first static position to a second static position, the improvement wherein said coupling means for coupling the rod with the piezoelectric reed comprises a generally rectangular tablet of insulating material, said tablet having a plurality of holes traversing the tablet perpendicular to its largest surface, one of said holes being tapped to engage a corresponding thread formed on said rod, the rest of said holes being freely traversible by other rods, and a slot communicating the tapped hole with one of the smaller surfaces of the tablet so as to provide a gripping effect by the periphery of the tapped hole on the threaded rod.

2. Device according to claim 1 wherein the width of said slot is less than a quarter of the diameter of said tapped hole.

3. Apparatus for transferring and recording written or printed information characters to or from a relief read-out panel and a magnetic tape comprising
   means monitoring the information characters and generating a signal output,
   means sending signals generated from said characters adapted for recording on the magnetic tape to a relief display device,
   a support housing including a tactually scanable plate having a plurality of holes therethrough arranged in an array;
   a plurality of electromechanical transducer devices having a longitudinal axis housed in said housing,
   each electromechanical transducer device comprising a bimorphous piezoelectric reed bendable around an axis perpendicular to its longitudinal axis on an application of a d.c. voltage,
   coupling means supported on said reed including a slot extending from an aperture to an edge thereof, and
   a rod arranged transversely to said piezoelectric reed and coupled to said coupling means, said rod having an end traversing slidably a respective corresponding one of said holes between a first static position in which said rod end projects a tactually detectable distance from its hole and a second static position in which said rod end does not project from its hole by the application of said d.c. voltage to said piezoelectric reed.

4. Apparatus for transferring and recording written or printed characters onto magnetic tape according to claim 3, comprising (1) means feeding said tape through a magnetic tape read-out head to generate signals, (2) means sending said signals to a decoding interface, (3) means sending said decoded signals to a memory until there is a predetermined accumulation of characters, and (4) means sending said accumulated characters to said relief display device.

5. Method of readout of magnetic tape bearing data in Braille-generable form comprising:
   (1) feeding said tape through a magnetic tape read-out to generate signals, (2) sending said signals to a decoding surface, (3) sending said signals to a memory until there is a predetermined accumulation of characters, and (4) sending said accumulated characters to said relief display device comprising: a support housing including a tactually scanable plate having a plurality of holes therethrough arranged in an array; a plurality of electromechanical transducer devices housed in said housing, each electromechanical transducer device comprising a bimorphous piezoelectric reed bendable around an axis perpendicular to its longitudinal axis on the application of a d.c. voltage, support means for at least one end of said reed, coupling means supported on said reed, and a rod arranged transversely to said piezoelectric reed and coupled to said coupling means, said rod having an end traversing slidably a respective corresponding one of said holes between a first static position in which said rod end projects a tactually detectable distance from its hole and a second static position in which said rod end does not project from its hole by the application of a d.c. voltage to said reed.

6. A relief display device comprising an electromechanical transducer device according to claim 1.

7. A portable electronic computer comprising a relief display device according to claim 6.

8. An apparatus control panel comprising a Braille keyboard and a display device according to claim 6.

9. In an information processing device, an electromechanical transducer according to claim 1.

10. A portable minicassette magnetic tape player/recorder comprising in combination: a Braille key board; a tape transport unit; a control circuit and a relief display device according to claim 6.

11. A method of fabricating an electromechanical transducer device including a tablet for coupling a bimorphous piezoelectric reed bendable around an axis perpendicular to the longitudinal axis of the reed upon the application of a DC voltage thereto to a rod arranged transversely to said piezoelectric reed comprising the steps of:

forming a threaded portion on said rod,
providing a generally rectangular tablet of insulating material having a plurality of holes traversing the tablet perpendicular to its largest surface,
slotting said tablet from one of said holes to one of the smaller surfaces of said tablet, and
tapping said one hole for threaded engagement with said threaded portion on said rod so as to provide a gripping effect by the periphery of the tapped hole on said rod threaded portion.

12. A method in accordance with claim 11 wherein said slotting step is carried out by a molding operation.

13. A method in accordance with claim 11 wherein said slotting step is carried out by a cutting operation.

14. A method in accordance with claim 11 wherein said step of forming a threaded portion on said rod is carried out by a knurling operation.

15. Apparatus in accordance with claim 3 including means monitoring the recording by generating a display in Braille characters from the data being recorded.

16. Apparatus of recording in accordance with claim 15 including means packaging the magnetic recording.

17. An electromechanical transducer device for a relief display panel comprising, in combination, a bimorphous piezoelectric reed bendable around an axis perpendicular to the longitudinal axis of the reed upon the application of a DC voltage, said reed being disposed substantially perpendicular to said panel, support means for at least one end of said reed, coupling means supported on said reed including a slot extending from an aperture to an edge thereof, a rod coupled to said piezoelectric reed through said coupling means and extending substantially parallel to said reed and means for applying a DC voltage to said reed whereby upon the application of said voltage, the bending of said reed causes static displacement of said rod in the direction of its own longitudinal axis substantially parallel to said reed.

* * * * *